(12) United States Patent
Martin et al.

(10) Patent No.: US 8,383,294 B2
(45) Date of Patent: *Feb. 26, 2013

(54) SELECTIVE HOLOGRAM FORMATION

(76) Inventors: Suzanne Martin, Blanchardstown (IE);
Izabela Naydenova, Dublin (IE);
Vincent Toal, Balbriggan (IE)

( * ) Notice: Subject to any disclaimer, the term of this patent is extended or adjusted under 35 U.S.C. 154(b) by 246 days.

This patent is subject to a terminal disclaimer.

(21) Appl. No.: 12/306,639

(22) PCT Filed: Jun. 29, 2007

(86) PCT No.: PCT/EP2007/056609
§ 371 (c)(1),
(2), (4) Date: Apr. 23, 2009

(87) PCT Pub. No.: WO2008/003661
PCT Pub. Date: Jan. 10, 2008

(65) Prior Publication Data
US 2009/0246642 A1 Oct. 1, 2009

(30) Foreign Application Priority Data
Jul. 3, 2006 (GB) .................................. 0613084.3

(51) Int. Cl.
*G03H 1/02* (2006.01)
(52) U.S. Cl. ........................... 430/1; 430/2; 359/3
(58) Field of Classification Search ........................ None
See application file for complete search history.

(56) References Cited

U.S. PATENT DOCUMENTS

| | | | | |
|---|---|---|---|---|
| 2,907,675 A | * | 10/1959 | Gaylord | 427/498 |
| 3,090,664 A | * | 5/1963 | Cline et al. | 8/115.53 |
| 3,427,161 A | * | 2/1969 | Delzenne et al. | 430/287.1 |
| 3,580,657 A | * | 5/1971 | Sheridon | 359/3 |
| 3,636,836 A | * | 1/1972 | Maddox et al. | 396/546 |
| 3,658,526 A | * | 4/1972 | Haugh | 430/1 |
| 3,660,091 A | * | 5/1972 | Shankoff et al. | 430/1 |
| 3,963,490 A | * | 6/1976 | Graube | 430/1 |

(Continued)

FOREIGN PATENT DOCUMENTS

| | | | |
|---|---|---|---|
| EP | 297051 | * | 12/1988 |
| JP | 56-125735 | * | 10/1981 |

(Continued)

OTHER PUBLICATIONS

Close et al., "holographic lens for pilot's head-up display", NTIS publication AD-787 605 (Aug. 1974).*

(Continued)

*Primary Examiner* — Martin Angebranndt
(74) *Attorney, Agent, or Firm* — Martensen IP; Michael C. Martensen

(57) ABSTRACT

We propose a method of detecting the presence of certain chemical and biochemical substances by virtue of the fact that they are, or have attached to them, either a dye molecule which acts as a photosensitizer for a holographic recording process, or another essential molecular component of the holographic recording material such as a monomer or a free radical generator. A recording material used in the process utilizes a photopolymer system consisting of a monomer and a crosslinking monomer, a free radical generator, a photosensitizer and, additionally, a polymeric binder when dry formulations are required and specifically lacks the substance to be detected. Subsequent holographic exposure records an interference pattern only where the complementary substance is present. Applications are broad ranging. Examples in diagnostics, printing, security, and environmental monitoring are given.

18 Claims, 12 Drawing Sheets

U.S. PATENT DOCUMENTS

| | | | | |
|---|---|---|---|---|
| 4,173,474 A | * | 11/1979 | Tanaka et al. | 430/1 |
| 4,187,111 A | * | 2/1980 | Chandross et al. | 430/2 |
| 4,422,713 A | * | 12/1983 | Grant et al. | 359/3 |
| 4,788,242 A | * | 11/1988 | Takahashi et al. | 524/459 |
| 4,842,968 A | * | 6/1989 | Kojima et al. | 430/1 |
| 4,942,102 A | * | 7/1990 | Keys et al. | 430/1 |
| 4,970,129 A | * | 11/1990 | Ingwall et al. | 430/1 |
| 5,196,282 A | * | 3/1993 | Knobbe | 430/2 |
| 5,296,305 A | * | 3/1994 | Baude et al. | 428/520 |
| 6,060,256 A | | 5/2000 | Everhart et al. | |
| 6,689,316 B1 | * | 2/2004 | Blyth et al. | 422/400 |
| 6,909,528 B2 | * | 6/2005 | Korzinin et al. | 359/3 |
| 2006/0222960 A1 | * | 10/2006 | Ueda et al. | 430/1 |
| 2007/0171491 A1 | | 7/2007 | Millington | |

FOREIGN PATENT DOCUMENTS

| | | | |
|---|---|---|---|
| JP | 61-265784 | * | 7/1986 |
| JP | 03-266433 | * | 11/1991 |
| JP | 2004-001514 | * | 1/2004 |

OTHER PUBLICATIONS

Kubota et al., "Methods of increasing the sensitivity of methylene blue sensitized dichromated gelatin", Appl. Opt., vol. 18(15) pp. 2538-2539 (Aug. 1979).*

Wang et al., "Wavelength-division multiplexing and demultiplexing on locally sensitized single mode polymer microstructure waveguides", Opt. Lett., vol. 15(7) pp. 363-365 (Apr. 1990).*

Volkov et al. "laser structuralization of gelatin with acrylic acid compound for producing high resolution sensitive media for hologram optics.", Appl. Opt. vol. 31(8), pp. 1053-1058 (Mar. 1992).*

PCT International Search Report PCT/EP2007/056609; Sep. 22, 2008.

* cited by examiner

Active dye in pen ink

Photopolymer surface

Holographic writen image

Active dye ink pad

Photopolymer surface

Holographic Fingerprint

Active dye in paint

Photopolymer surface

Holographic drawing

SELECTIVE HOLOGRAM FORMATION

FIELD OF THE APPLICATION

The present application relates generally to the field of holography. More particularly, the present application relates to a method for creating holograms and the use of holographic recording media for sensing applications.

BACKGROUND TO THE APPLICATION

Holography is well known and widely used in many commercial applications including display holography, security, advertising and holographic optical elements and gratings. A holographic image is produced when light is diffracted at a complex spatially varying diffraction grating, which, in the simplest terms, re-directs the light towards the viewer in such a way as to give the illusion that the light is coming from a solid three-dimensional object.

This diffraction grating is produced by exposing a suitable photosensitive material to the optical interference pattern produced when two coherent light beams (usually produced by a laser) meet. The material records the variation in light intensity (as a variation in refractive index, absorption or thickness) and a corresponding diffraction grating results. If both light beams are simple collimated beams, the result will be a simple diffraction grating whose spatial period depends on the angle between the recording beams.

If the diffraction grating is illuminated with one of the recording beams (or a similar beam) it will diffract the light to reproduce the other recording beam. If one of the beams is a complex wavefront coming from a three dimensional object, the recorded diffraction grating will have the property that it can reconstruct this wavefront when illuminated with the other beam.

A wide variety of photosensitive materials are available including photopolymers, silver halides, dichromated gelatin, photo resists, thermoplastics, photochromics and photorefractive materials.

The recording process in photopolymers is described in detail in later sections.

Silver halide emulsions are widely used as holographic recording materials because of their sensitivity and their commercial availability. In addition these materials can be dye sensitized so that their spectral sensitivity matches the most commonly used laser wavelengths. These emulsions are suitable for recording amplitude and phase holograms, and can be used in transmission or reflection mode. A drawback of silver halide emulsions is that they need wet processing and drying.

Dichromated gelatin (DCG) consists of a gelatin layer impregnated with ammonium dichromate. Depending on the development techniques, the hologram can be recorded as a thickness variation or refractive index modulation. Similar to the silver halide emulsions, DCG can be dye sensitized. Among its advantages are large refractive index modulation capability, high spatial resolution, and low scatter. A main disadvantage is the requirement for post recording processing.

Photoresists are light sensitive organic films that yield a surface relief image after exposure and development. Photoresists can also be dye sensitized. Main drawbacks of these holographic recoding materials are the low sensitivity and the post recording processing. Their primary advantage is their low scattering resulting in high spatial frequency resolution.

In addition to these materials for irreversible holographic recording there are a number of materials that may be used several times. Such materials are thermoplastics, photochromic materials undergoing reversible changes in colour when exposed to light, photorefractive materials undergoing change in the refractive index due to light induced charge redistribution resulting in space modulated charge field and photoanisotropic holographic recording materials for polarization holography.

Conventionally, the photosensitive material is prepared as a film or solid layer on a substrate. Since the materials are generally photosensitive, once prepared, they are typically stored in the dark until required for use.

Holograms have been used in a number of different sensing applications. For example, Smart Holograms Ltd. of Cambridge, UK have proposed a number of Holographic sensors for detection of a variety of conditions including moisture, alcohol and analytes. The general principle of detection employs a change in the optical characteristics of already existing hologram. Generally, these sensors employ a preformed hologram formed with a support medium. The support medium is analyte sensitive. In use, a physical property of the hologram support medium is altered by the reaction of the analyte in liquid form with a substance disposed throughout the sensor. This in turn causes a variation of one or more optical characteristics of the hologram, which is detectable. The physical property of the holographic element (principally formed using silver halide based films) which alters may, for example, be its volume, shape, density, viscosity, strength, hardness, charge, hydrophobicity, solvent swellability or integrity. The detectable variation arising from the alteration of the physical property is suitably a change in optical characteristics, including for example, polarisability, reflectance, refractance or absorbance of the holographic element. Examples of patent applications related to this include WO95/26499, WO2003/087899, WO2004/081546, WO99/63408, WO2006/008531 and WO2006/008524.

SUMMARY

In contrast to the prior art in which a photosensitive material is prepared or provided as a standard step with the primary process concerned with the production of a hologram in photosensitive material and the subsequent use of the hologram, the present application employs the principle that a hologram is not capable of being formed if the required photosensitive material is not actually photosensitive.

Alternatively stated, the present application employs the principle that if a photosensitive material comprises several essential constituents to be photosensitive these constituents may be detected by the absence of a hologram after a holographic recording process.

Positively stated, the presence of an essential constituent may be detected by the presence of a hologram. This principle may be employed in a variety of different ways, which will become apparent from the detailed description, which follows.

DETAILED DESCRIPTION OF DRAWINGS

Figure 1:
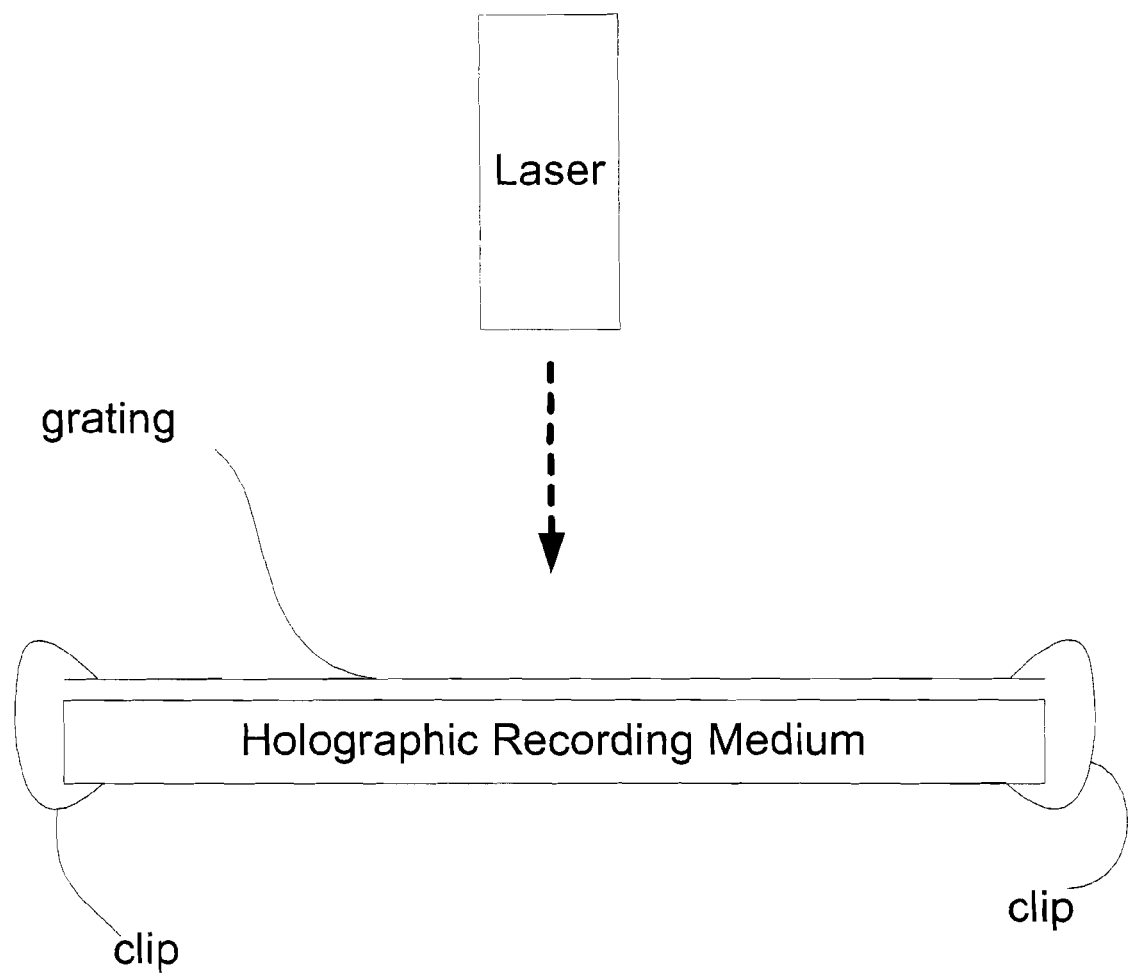
FIG. 1 represents a simple apparatus for recording a hologram on a holographic recording medium as might be employed with the prior art and with the technology of this application.

The present application will now be described exemplarily with reference to a holographic recording process employing photopolymers. It will be appreciated that the technique may also be applied to other holographic recording materials where an essential component may be omitted in the manner substantially described below. For example, the method may be applied to dye sensitised silver halide, dye sensitised DCG and dye sensitised photoresists. However, an inconvenience in using these holographic recording materials is the necessity of post processing.

In a conventional photopolymer hologram recording process a light pattern is produced by the interference of two or more beams of mutually coherent light incident upon a photosensitive layer containing a photosensitive dye. The photosensitive layer typically comprises a number of individual components including: a dye, a free radical generator, a monomer and, optionally, a binder. Although, it will be appreciated that there may be more than one type of each component, e.g. several different monomers or several different dyes may be employed in the photosensitive material. The role and nature of these materials and the process by which they combine to record a hologram will now be discussed briefly. Although, it will be appreciated that these techniques would be well known and understood by those skilled in the art.

The role of the photosensitive dye in the photosensitive layer is to absorb light and start the photochemical processes that lead to holographic recording. Examples of photosensitive dye would include erythrosine B, fluorescein and other xanthene dyes.

In bright regions of the produced interference pattern, the energy from photons of light raises the dye molecules to excited singlet states. Many of the singlet state excited molecules are then converted to triplet state excited molecules by intersystem crossing. In the triplet state, a dye molecule can interact with a free radical generator, for example, triethanolamine. This interaction produces an active free radical. The active free radical can, in turn, interact with a monomer molecule such as acrylamide creating a monomer radical. The creation of the monomer radical, results in free radical polymerization occurring in the polymer material.

Conversion of the carbon-carbon double bond to a single bond changes the molecular polarizability of the acrylamide and thus its refractive index. In addition, the depletion of monomer concentration in illuminated regions results in a spatial gradient of monomer concentration inducing diffusion of monomer from dark to bright regions. This process also contributes to a local change in refractive index. By these mechanisms, the spatial variation in light intensity is recorded as a refractive index variation in the photopolymer layer, i.e. a hologram is produced.

The dye, free radical generator and monomer may all be considered as being essential to the photosensitive material or more generally to the process of recording a hologram, since, if any are absent, photopolymerisation cannot take place. This characteristic is employed in the sensing/detecting process of the present application.

In particular, the method comprises providing an inactive holographic recording material. In the context of the present application, an inactive holographic recording material means a material capable of recording a hologram once activated. It will be appreciated, that activation is the providing of one or more essential components substantially absent from the inactive recording medium, which are required to transform the inactive material into an active material capable of recording a hologram.

In particular, the present application uses the principle that only when a missing component, e.g. dye, monomer or free radical generator is introduced to an inactive layer containing all the other essential components does photopolymerisation become possible. In the event that the missing component is not introduced attempts to create a hologram using the light recording technique described above will fail. In contrast, if the missing component is present a hologram will result.

The photopolymerisation process described above is by nature an amplification process, insofar as one dye molecule can facilitate the polymerization of many generator as the essential component to be detected. Moreover, depending on the application, it may be most advantageous to select the dye as the essential component to be detected.

If the presence of the missing essential component is dependent on the presence of a further component, then obviously the production of a hologram will indicate the presence of not only the missing essential component but also the further component.

A more detailed explanation now follows with reference to an exemplary embodiment for a sensing system for detecting the presence of dye.

The exemplary sensing system comprises (1) a polymer layer designed to be capable of recording a self-developing hologram only if a dye is present and (2) a simple apparatus for on the spot recording of holograms.

The photopolymer holographic recording material (discussed below in greater detail), which has been developed at the Centre for Industrial and Engineering Optics, Dublin Institute of Technology, may be provided as a layer of material, possibly on a solid substrate such as a glass slide, with the exception that the dye is omitted from the formulation of the holographic recording material. The omission of the dye from the formulation renders the final layer inactive i.e. substantially incapable of responding to light. Efforts to record a hologram by exposure to an interference pattern will not be successful unless dye is introduced.

In greater detail, the inactive holographic recording medium suitably comprises a photopolymer layer composition comprising the following: a binder, which acts as a support medium or host matrix for monomers and a free radical generator.

In more detail, the structure of an exemplary holographic recording medium, which has been found to provide good results, includes the following:

Monomer:

An exemplary monomer used in the photopolymer composition is acrylamide. The carbon-carbon double bond (C═C). This double bond is broken on polymerization resulting in two single bonds. In particular, electrophoresis grade acrylamide powder (for example, as available from Sigma Aldrich of St Louis, Mo., USA) may be used.

$$CH_2\!=\!\underset{H}{\overset{}{C}}\!-\!\underset{O}{\overset{}{C}}\!-\!NH_2$$

Binder:

A suitable binder used in the photopolymer layer is polyvinyl alcohol (PVA) (for example from Sigma Aldrich or Riedel De Haen). The chemical formula for pure polyvinyl alcohol (100% hydrolyzed) binder is shown below.

$$-\!(CH_2CH)_n\!-\!\underset{OH}{|}$$

A low percentage hydrolysis binder may also be used. The chemical formula of an alternative lower percentage hydrolyzed polyvinyl alcohol in which a second polymer (generally polyvinyl acetate, from which the polyvinyl alcohol is synthesized) is as follows polyvinyl alcohol    polyvinyl acetate $$-\!-\!-\![CH_2\!-\!\underset{OH}{\overset{|}{CH_2}}]_n\!-\!-\![CH_2\!-\!\underset{COO-CH_3}{\overset{|}{CH}}]_n\!-\!-\!-$$

Crosslinking Monomer:

A second monomer employed in the exemplary photopolymer layer composition acts as a crosslinking monomer, for example NN'methylenebisacrylamide (available from Sigma Aldrich). The structure of the molecule is shown below. It is a symmetric molecule of two acrylamide molecules attached with a methyl group in the middle.

Free Radical Generator:

An exemplary free radical generator comprises Triethanolamine (TEA) (available from Sigma Aldrich chemicals). As explained above, the free radical generator plays a significant role in the generation of free radicals to initiate a polymerization reaction. The chemical formula of TEA is shown below.

$$N(CH_2CH_2OH)_3$$

A method of preparation of an exemplary suitable (inactive) polymer recording layer comprises some or all the following steps:

Stock Solution of Polyvinyl Alcohol (PVA):

10 grams of PVA of specified molecular weight and hydrolysis is dissolved in 100 ml of water to prepare a 9.1% by weight or 10% w/v PVA solution.

Composition of Photosensitive Medium:

A composition of the photosensitive medium is prepared by adding 2 ml of triethanolamine to 0.2 grams of NN'methylenebisacrylamide (crosslinking monomer) and 0.6 grams of acrylamide (monomer). To this mixture, 17.5 ml of stock solution of 9.1% polyvinyl alcohol is then added and the total solution is stirred thoroughly, to ensure the monomer and crosslinking monomer are completely dissolved to obtain a homogenous solution.

Layer Preparation:

1.5 ml of photopolymer solution is spread uniformly on a 50×50 mm$^2$ glass plate placed on a leveled surface and allowed to dry forming a film. The drying time is usually 36-48 hours. The thicknesses of the photopolymer film layers thus formed are approximately 120 μm to 140 μm. The layer may also be used in liquid form, when higher concentrations may be used There are many variations in concentration and volume of the above formula, which also work well. For example, where more brightness is required in the final holographic image more acrylamide can be used and where lower angular selectivity is an advantage, much thinner layers are prepared. Much thicker samples and larger area samples may also be prepared. Samples may also be prepared in any desired shape by moulding.

It will be appreciated that alternative monomers, free radical generators and binders may be employed depending on the particular requirements of the application. Similarly, additional components, for example, nanoparticles may be added for improved performance.

Alternative monomers would include any suitable monomers such as acrylamides, for example: N,N-Diethyl acrylamide, Tradename: DEAA; N,N Dimethyl acrylamide, Tradename: NNDMA; N-Isopropyl acrylamide, Tradename: NIPAM; N-(2-Hydroxyethyl acrylamide), Tradename: HEAA; or 2OHydroxyethyl methacrylate, Tradename-HEMA. Similarly, the monomer may comprise an acrylate such as: N,N Dimethylaminoethyl Acrylate; or N,N Dimethylaminoethyl Methacrylate Exemplary alternative binders could include Poly vinylpirrolidone; a sol-gel; a hydrogel; an acrylate: Polyethyleneoxide: Polyethyleneglycol: and Polyethyloxazine.

Exemplary alternative free radical generators may include N-phenilglycine (NPG) which may be used in combination with Diphenyliodonium Hexafluorophosphate (DPI).

Once the layer of inactive holographic recording material has dried (if not being used in liquid form or gelatinous form), it may be exposed to a holographic recording process. If sensitizer is not present, no hologram will result. Similarly, if the sensitizer is present in an area a hologram will result in that area.

In this respect, the sensitizer (also referred to as a dye or as a dye sensitizer) is suitably a photosensitive dye, for example Erythrosin B (available from Sigma Aldrich chemicals). Erythrosin B is green light sensitive dye having a complex structure with four benzene rings. The structure of the molecule is shown below.

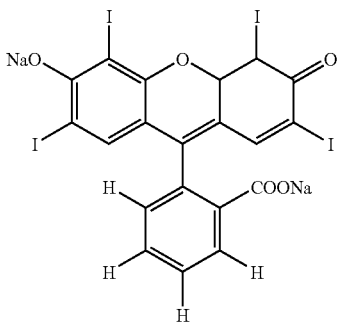

Alternatively, a wide variety of sensitizers may be used, including for example: Erythrosin B; Methylene blue; Eosin; Eosin yellowish; Fluorescein; any xanthene dye; or a thionine dye. The dye can be introduced to the polymer layer or liquid by deposition in solution or solid form, by contact with a dye impregnated dry layer, or by a printing or spraying process.

This is also true of molecules to which the dye is attached and substances in which the dye is a constituent regardless of whether they are solid or liquid.

To detect if the dye is present a simple apparatus may be employed for 'on the spot' recording of holograms or gratings.

Such an apparatus is shown in FIG. 1 and comprises a grating which is placed in contact with the recording layer described above. Light from a coherent light source such as a diode laser is oriented so that it illuminates the polymer layer through the separately). The role of the grating is to produce a second beam which will interfere with the first beam coming from the light source. As the two beams are coherent this will produce an interference pattern in the area of overlap of the two beams. Alternatively the second beam could be produced with the help of a mirror or a prism. Suitable retention means may be provided comprising clips or a slotted support arrangement to ensure that the grating, light source and recording layer are fixed relative to one another. Illumination of the photopolymer layer through the grating will record a holographic grating if the photopolymer layer has been suitably sensitized (by the presence of dye). The amount of exposure of the photopolymer layer through the grating is selected to be such that a holographic grating will be recorded if the photopolymer layer has been suitably sensitized. This exemplary apparatus may be scaled to the appropriate size for a particular application. Tunable or multiple light sources or a system of filters may be employed for multiplexing purposes so that more than one analyte may be detected.

So if a substance is brought into contact with the inactive polymer layer described above, and subsequently exposed by the recording system above, a holographic grating will form only if dye is present. Thus, the presence (or absence) of dye is detected by virtue of the fact that a holographic grating is formed (or not formed). The strength of the recorded holographic grating will depend on the concentration of dye and its activity in terms of production of excited triplet states. Furthermore, it can be inferred that the molecules of interest are located where the holographic grating was formed. In this regard, the dye molecules may be bound to other chemical or biochemical analytes (i.e. labeled). The use of labeling allows for a wide variety of materials, molecules and compounds to be detected (further details of which will be described below). Some exemplary applications of the technology will now be described.

Figure 2A:
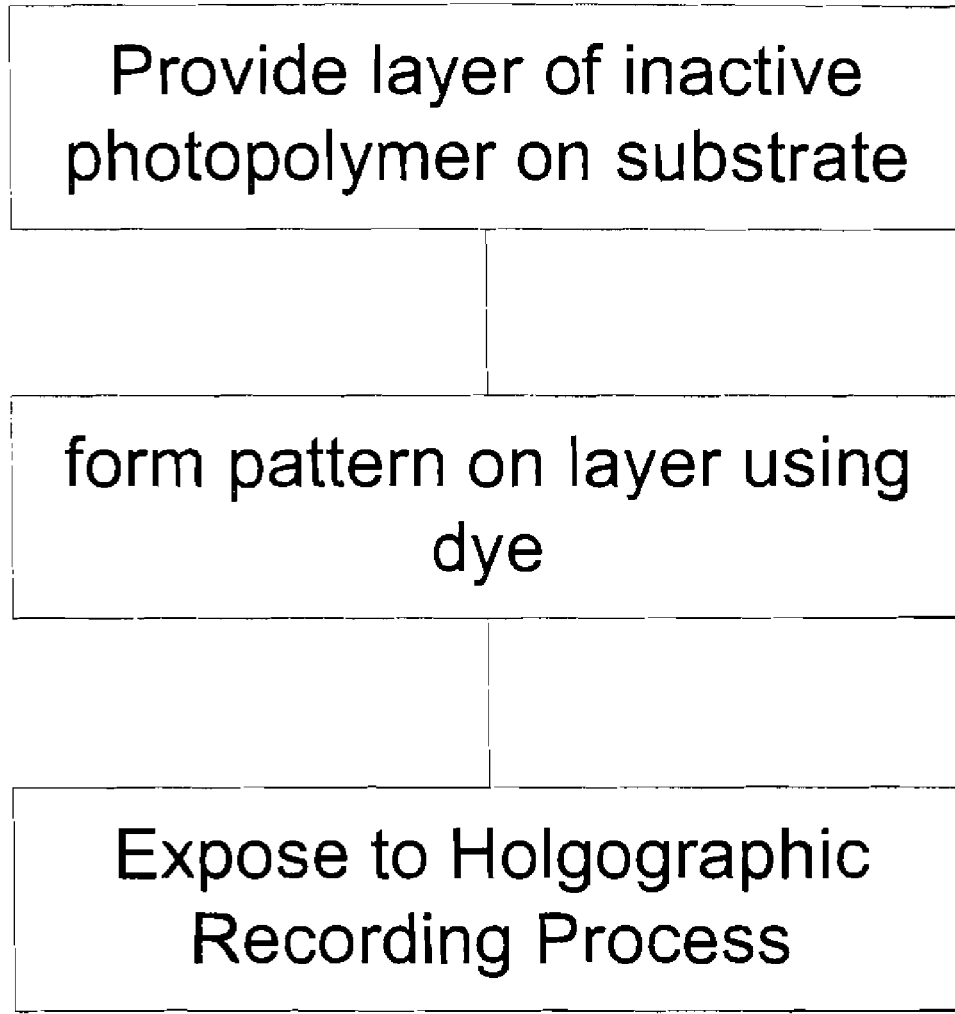
FIG. 2A is an exemplary process flow according to an embodiment of this application.
Figure 2B:
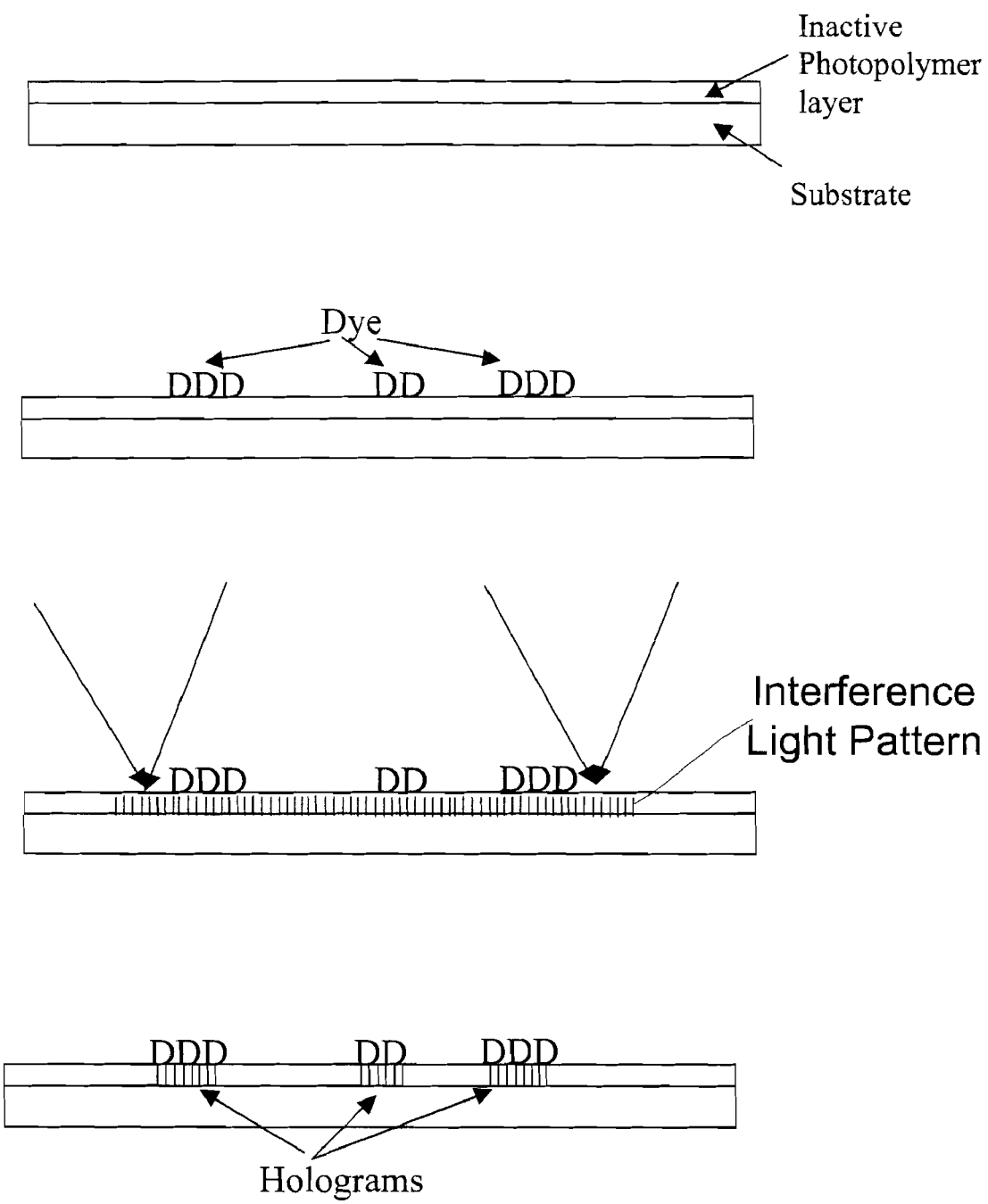
FIG. 2B represents the results of each of the steps of the process flow of FIG. 2A.

In a first exemplary method, shown in the process flow of FIG. 2A, a first step provides an inactive holographic recording medium, for example, as a layer upon a substrate. The substrate may for example be glass or plastic. A pattern is then defined upon the layer of inactive material by the selective application of dye as depicted in FIG. 2B. The application of the dye activates the regions of the inactive layer where recording process, e.g. using the apparatus described above, results in a holographic pattern confined to those areas defined by the selective application of the dye. This method has a wide variety of uses for security, authentication and graphical design and printing purposes.

Figure 3:
FIG. 3 is a pictorial representation of another embodiment of this application.
Figure 3:
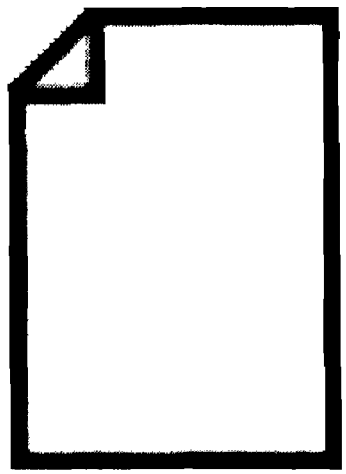
Figure 3:
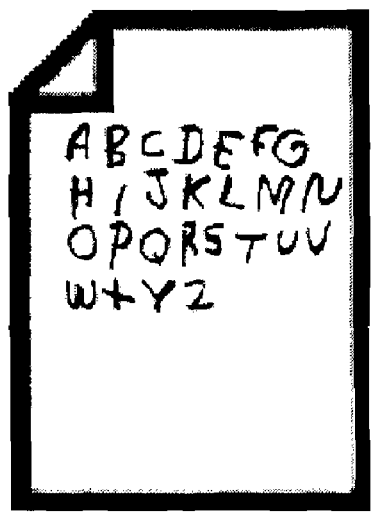

For example, in a first method, the inactive holographic recording medium may be provided, as shown in FIG. 3, in a format suitable for writing upon. In one example, the inactive holographic recording medium may be provided as the signature strip on the back of a payment card or as part of an identification document (e.g. passport or driver's license) or even as a corporate or official stamp on merchandise or stationary. Before general use, the cardholder signs the card using an ink comprising dye. The card may then be exposed using, for example, the simple holographic recording apparatus described above. Once completed, the cardholder's signature is recorded as a hologram. It will be appreciated that such a signature may be harder to interfere with or alter compared to a conventional ink based signature.

Figure 4:
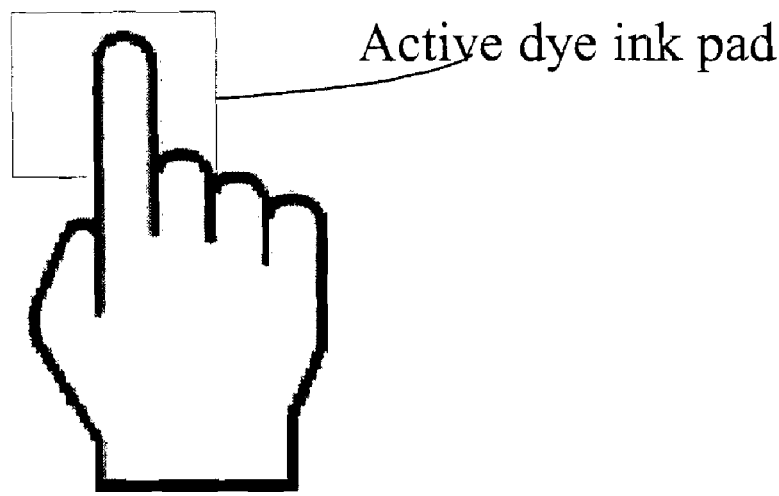
FIG. 4 is a pictorial representation of a further embodiment of this application.
Figure 4:
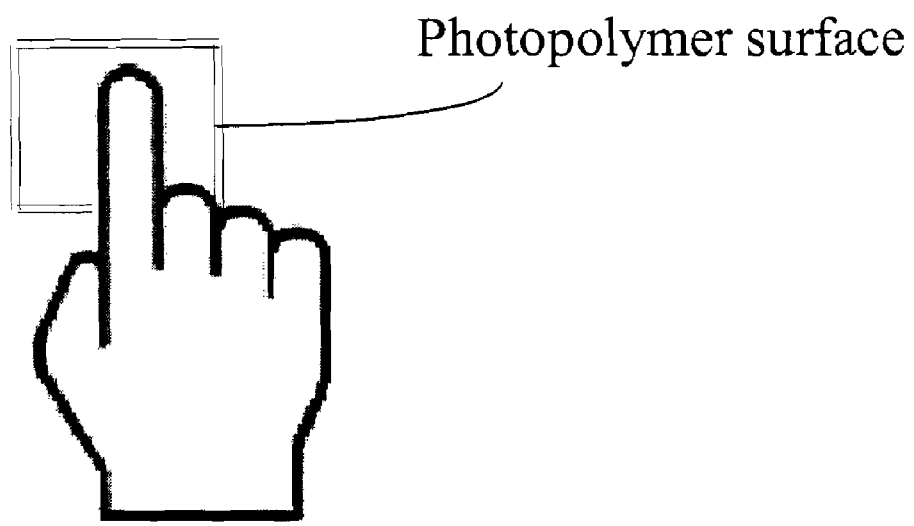
Figure 4:

Similarly, as shown in FIG. 4, in place of a signature on an identification card, the identification card might have a larger area of inactive holographic material (corresponding to the size of a fingerprint). In use, a user might stamp their finger in an inking pad holding dye and then impress their finger upon the area of inactive holographic recording medium. Exposure using the simple holographic recording apparatus described above results in the recording of the user's fingerprint as a hologram. The process could also be used to authenticate stamps and seals.

Figure 5:
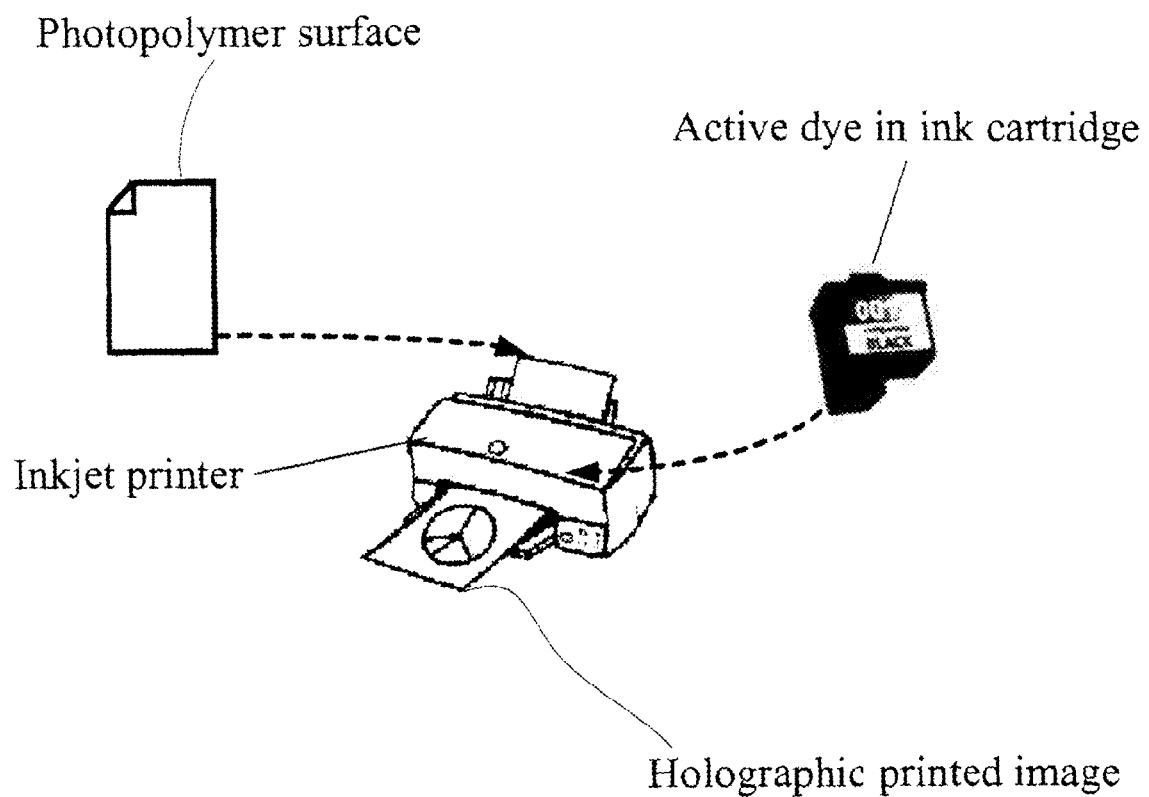
FIG. 5 is a pictorial representation of yet a further embodiment of this application.

It will be appreciated that a variety of other uses of this process may be employed for security and authentication. In this regard, the dye may be provided in much the same way as other inks. For example, as shown in FIG. 5, the ink is provided in an ink jet printer for use in an ink jet printing process. In such an arrangement, a holographic feature may be provided in any printed pattern (e.g. a company logo) which when exposed to a holographic recording process provides a significantly enhanced level of authenticity and security over a simpler ink printed document.

The resulting holograms may be selected to be overt (i.e. visible to the naked eye) and\or covert (i.e. requiring special equipment to be seen, e.g. operable only in infrared region of spectrum).

These security features in effect reveal the presence of the dye in areas where the dye has been deposited upon the inactive holographic recording material and a subsequent holographic recording has been employed to create a holographic pattern on the resulting pattern of activated material.

Figure 6:
FIG. 6 is a pictorial representation of yet another embodiment of this application.
Figure 6:
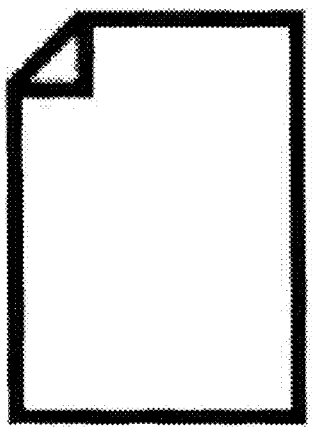
Figure 6:
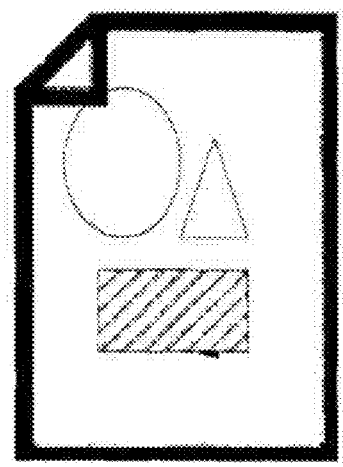
Figure 7:
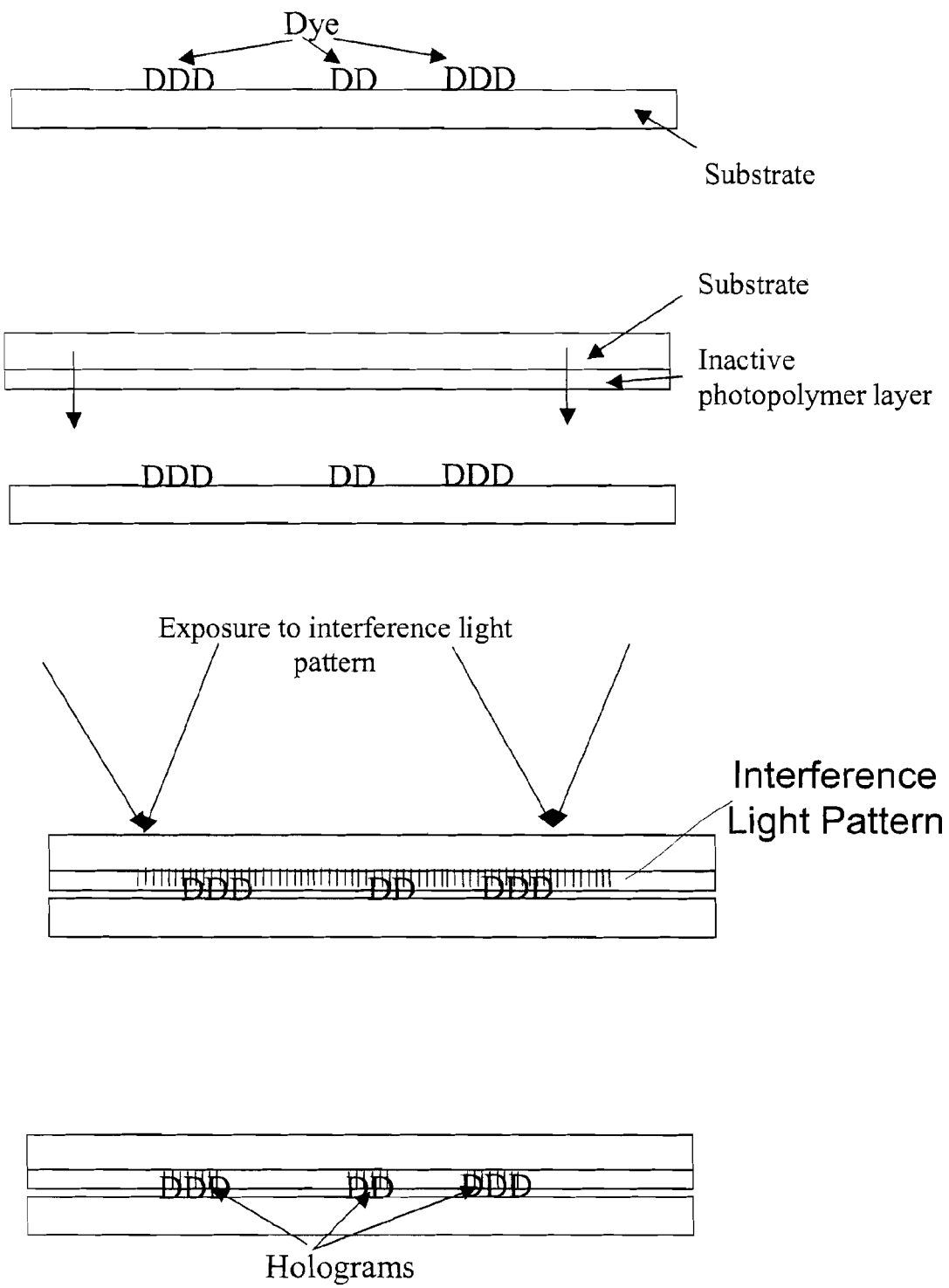
FIG. 7 represents the results of an alternative process flow to that of FIG. 2A.
Figure 8:
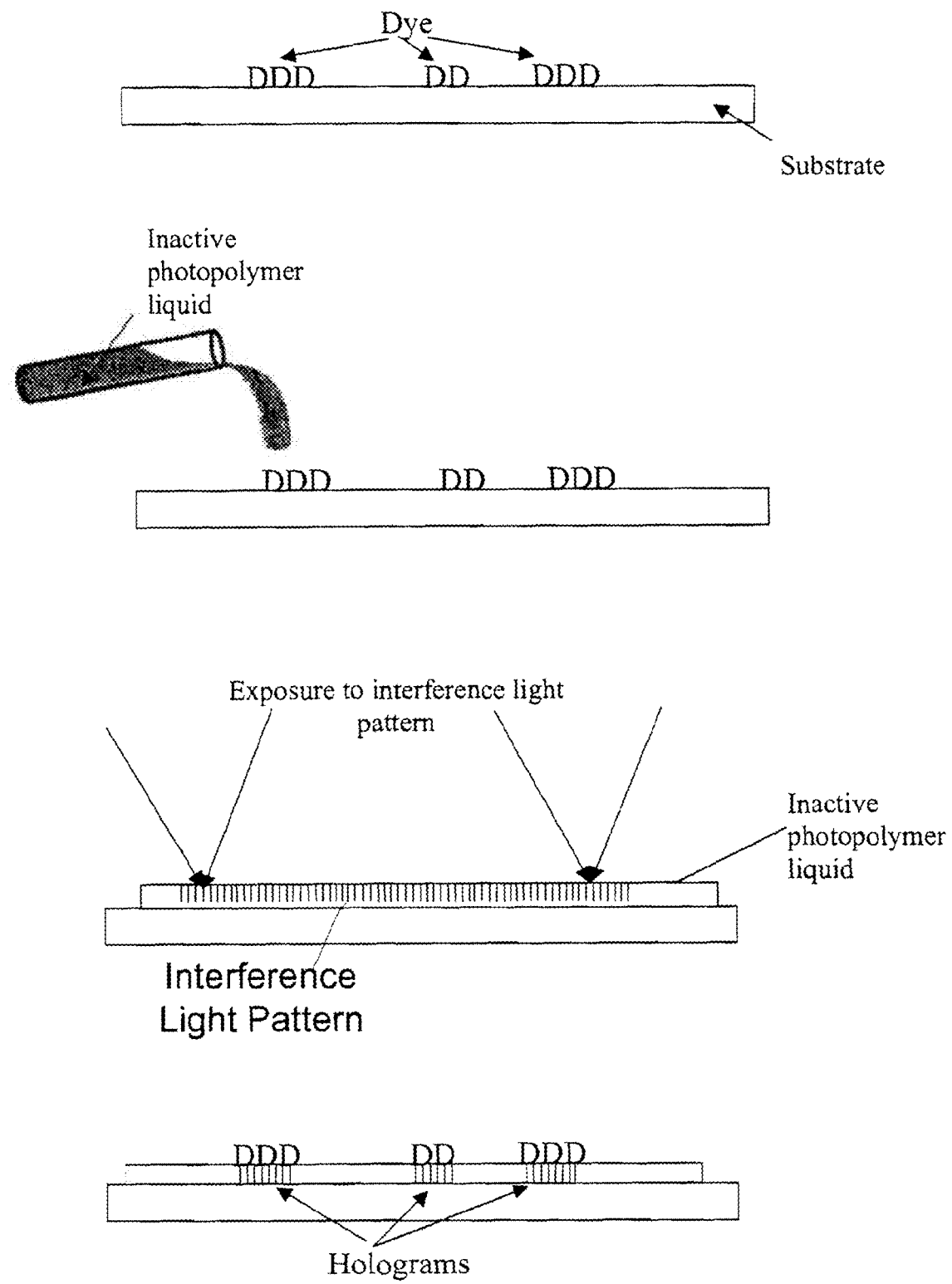
FIG. 8 represents the results of yet another alternative process to that of FIG. 2A, FIG. 9 demonstrates a further exemplary embodiment in which a nucleic acid may be identified by the present application.
Figure 9:
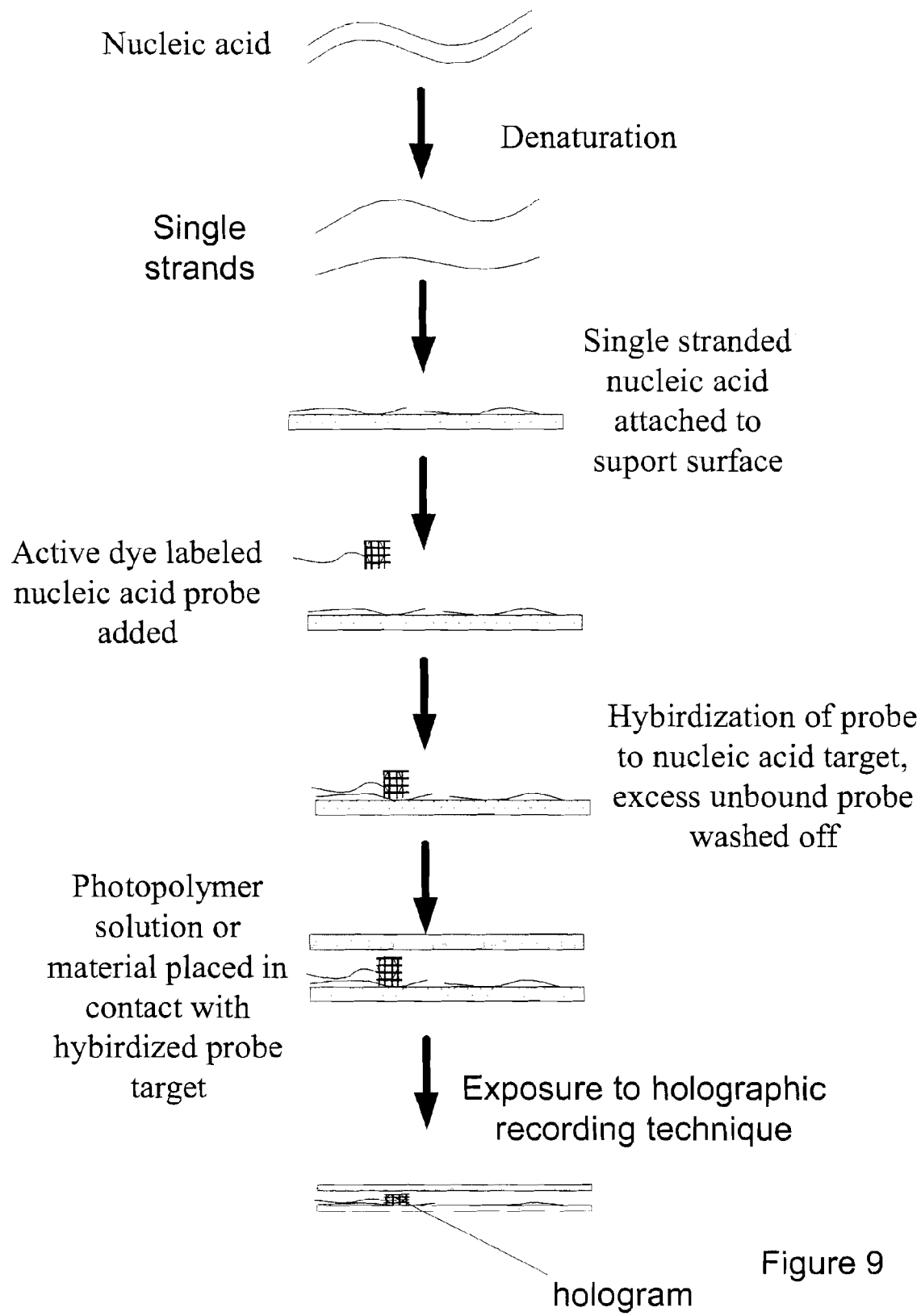

It will be appreciated that a wide variety of other applications are possible by the selective application of an essential component to an otherwise inactive holographic recording medium. For example, the dye might be used as a paint by an artist upon a canvas comprising a layer of inactive holographic recording material with the subsequent exposure to a holographic recording process resulting in a unique work of art as demonstrated by FIG. 6.

It will be appreciated that a fundamental aspect of this application is the bringing together of an inactive holographic recording material with one or more missing components required to activate the holographic recording material and the subsequent recording of a hologram. Accordingly, whilst the above exemplary embodiments describe providing the inactive holographic recording material as a first step and the subsequent provision of the missing components, it will equally be appreciated that the missing component, e.g. dye may be provided as a dry layer for example on a substrate, as shown in 7, as a first step with the inactive polymer provided on a second substrate which is brought into contact with the first substrate.

Similarly, it will be appreciated, that the missing component, e.g. dye may be provided as a dry layer for example on a substrate, as shown in 8, with the inactive holographic recording material subsequently being brought into contact with it (e.g. by pouring a liquid mixture of monomer and free radical generator onto a surface to which the dye is bound.

Photopolymerization and creation of a holographic diffraction grating at a particular location. The holographic grating is detected by its ability to diffract an incident light beam in the direction of a photodetector or the observer.

Biosensing applications are well known in the art and a wide variety of techniques are available for the detection of biological molecules such as for example enzymes, proteins and nucleic acids. One commonly employed technique employs fluorescence detection systems to identify labeled molecules. These techniques may readily be applied to the present system as the existing fluorescence detection techniques employ for example Xanthene dyes and other similar dyes (for detection by fluorescence detection systems). The present application may be adopted for such purposes to determine whether a labeled biomolecule is present in a solution by dropping the solution onto an inactive polymer layer and exposing the layer to a holographic recording process as described above. If a hologram/grating appears the biomolecule is present. If it does not the biomolecule is not present. In contrast to many fluorescence detection systems, the present application provides a permanent physical record, which can be interfaced with image recording, processing and storage devices. In addition, the result may be visible to the naked eye.

The following is an example of a somewhat more complex and versatile system which can also be used to test for a range of biomolecules. For simplicity we confine the example to Nucleic acid detection although it will be appreciated by those skilled in the art that it may be applied to a test for any biomolecule for which a suitable label is available.

In particular, the example of identifying a particular gene in a DNA sample will be considered. As with the prior art, the first step is the extraction of DNA from the nucleus of the cell sample. A number of different methods for performing this are known in the art, typically by use of an appropriate chemical. Once extracted, the sample is purified and denatured (separated) into single strands, the most commonly employed method for which is heating the DNA sample to 95° C. Once the DNA is purified and the strands denatured, the next stage is amplification to ensure a sufficient amount of sample to be detected and measured. Polymerase Chain Reaction (PCR) is a commonly applied technique for this. As part of the PCR amplification having a fluorescent dye attached. The complementary target strand will only bind with the strand being targeted for. The presence of the target strand may then be detected by fluorescent detection methods.

As an alternative to fluorescent detection the holographic recording process described above may be applied to gene identification. The exemplary sensor comprises a layer of inactive holographic recording material, as described above. In addition, in this exemplary embodiment, the layer further comprises DNA strands complementary to those to be identified.

Using techniques well known in the art, the sample to be tested has its DNA extracted and split into strands. Other processes such as purification and amplification, which are well known, may also be employed. If the inherent magnification of the method of the present application is sufficient, the step of amplification may not be required. Dye molecules may then be attached to the DNA strands of the sample as labels.

Once the labeled sample is brought into contact with the layer of inactive holographic material, complementary strands in the sample and on the inactive layer will bind and in effect be captured in particular locations. A washing step or steps may then be employed to remove unattached DNA and labels. This leaves the dye labeled molecules attached in specific locations on the inactive layer.

Exposure to a holographic recording process, as described above, will produce a hologram wherever the complementary strands (and accordingly dye) are present.

Thus for example, it would be possible to provide a microarray having a variety of different complementary strands corresponding to DNA to be identified. Each location in the array is primed to retain labels attached to different DNA strands to be identified. In this way, a single test could be used to identify the presence or absence of a plurality of different genes in a single process. It may also be advisable to include a reference spot. This reference spot is suitably provided with dye so that it may be used to verify that the holographic recording process has worked properly. In some arrangements, multiple active dyes may be labeled to different probes (multiplexing in space, in target and in time), the individual active dyes might be activated by the same checked with the development of a hologram. i.e. a dual detection system (fluorescent and holographic) might be provided.

This technology may be used in a broad range of bioassays and biosensors which are mainly fluorescence or phosphorescence based, i.e. where the holographic process replaces or complements the fluorescent or phosphorescent detection.

Applications would include nucleic acid, antibody, enzyme and ligand based assays, for example nucleic acid hybridization, PCR, DNA and protein microarrays, immunoassays, oxygen sensing assays and cell viability assays Application is also envisaged where fluorescence or phosphorescence is a key assay component in or by product of for example, fluorescent in situ hybridization, food (product) quality and integrity, pharmacokinetic analysis, toxicity screening, environmental analysis. In each case, the principle of operation will be the same, i.e. employing a label comprising an essential component of an otherwise inactive holographic recording material and attempting to record a hologram thereon.

Figure 10:
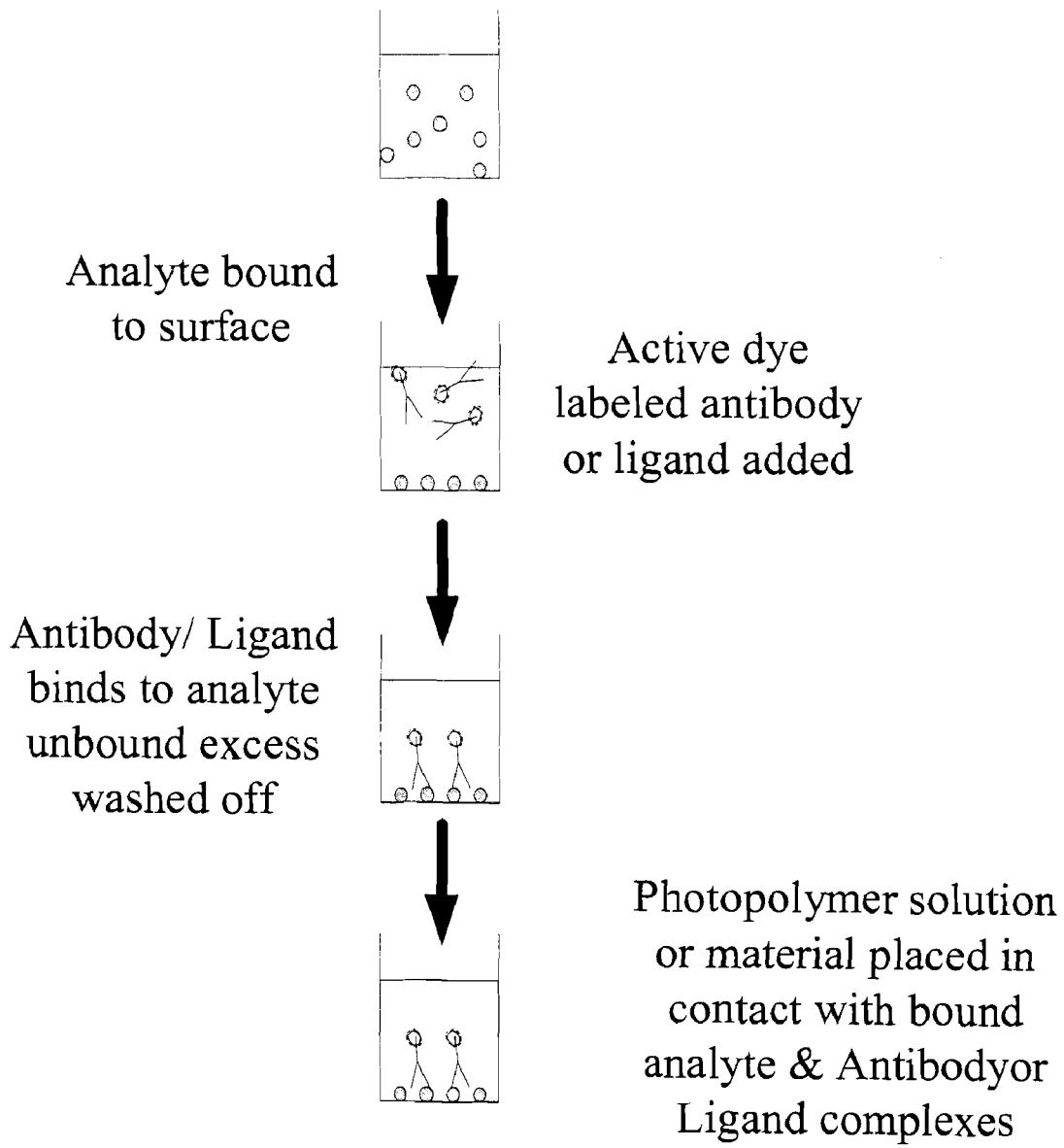
FIG. 10 represents an embodiment by which an analyte may be detected using a direct method of the present invention.

The method may also be employed for detecting particular analytes. An exemplary direct method for this will now be described with reference to FIG. 10, in which a first step provides the sample to be tested in a suitable container. A second step binds the analytes to the surface of the container. An active dye labeled probe (for example introduced. This probe binds with the analytes. A subsequent washing step removes any unattached probe. The inactive holographic recording material may then be introduced, for example in liquid form and the container exposed to a holographic recording process as described previously (not shown). Alternatively, the test solution may be poured onto a layer of the holographic recording material. The presence of a hologram indicates the presence of the analyte. The method is referred to as a direct method since the dye is attached directly (via the probe) to the analyte.

Figure 11:
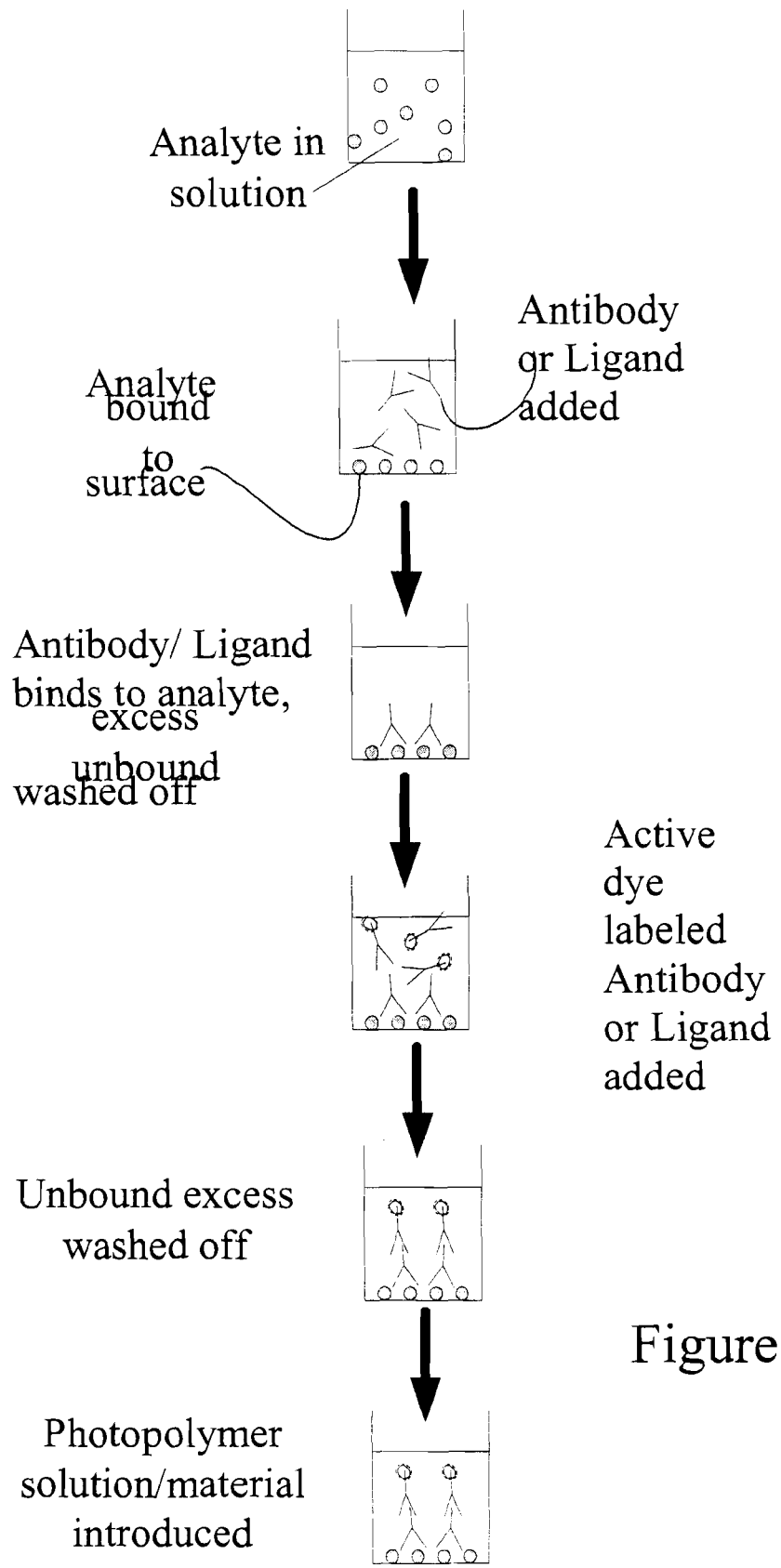
FIG. 11 represents an embodiment by which an analyte may be detected using a indirect method of the present invention.

An alternative approach is to employ an indirect method. In the indirect method, two probes are used, the first probe is used to target the analyte, with the second probe having a dye attached being used to target the first probe. An exemplary indirect method of detection is shown in FIG. 11. In the indirect method the primary probe could be nucleic acid, a substance, an antibody, a ligand etc. which targets the desired analyte. A washing step is employed to remove any of the unattached first probes. After washing, a second probe is introduced. The second probe may be an active dye labeled antibody or ligand which in turn targets the first probe. A further washing step removes any unattached second probe. The inactive holographic recording material may then be introduced, for example in liquid form. The holographic recording material may then be exposed to a holographic recording process as described previously (not shown). Alternatively, the test solution may be poured onto a layer of the holographic recording material. The presence of a hologram indicates the presence of the analyte. The method is referred to as an indirect method since the dye is attached indirectly to the secondary probe which binds to the primary probe which binds to the analyte. This also gives the potential for signal amplification as there may be multiple binding sites on the primary probe to which many secondary probes can bind.

The present application may be used in place of existing detection systems in any scenario where an active dye can take the place of the commonly used fluorescence and phosphorescence compounds. The photopolymer may take the place of or be complementary to commonly used fluorescent detection instrumentation, for example, such as spectrofluorometers, fluorescence microscopes, fluorescence scanners, microplate readers and flow cytometers.

The present application may also be used in environmental monitoring. Conventionally, fluorescent dyes are added to water sources so that the route of a water flow can be traced. Fluorescent detection (e.g. by shining a UV light) at a point suspected of being in the flow route confirms whether or not this is the case. Instead of sampling the water using fluorescence, a drop of the water sample may be placed on an inactive holographic material as described above and the holographic recording technique implemented. The holographic material may then be inspected to obtain an immediate determination of whether the dye was present in the sample or not.

Similarly, the sensor may also be configured for use in monitoring environmental conditions. In such an arrangement, the sensor may be provided as two parts. The first part having the inactive holographic recording material and the second having the material required to activate the holographic recording material. Suitably, the two parts are arranged so that they may be applied directly together. For example, each of the parts might be provided in tape form, which could be applied together. Alternatively, one of the parts might be provided as a solid layer on the packaging of the material to be monitored and the second part might be provided as a tape. In contrast to the earlier described methods in which exposure to the holographic recording process is a relatively immediate next step, the environmental sensor operates by whilst making the material active by putting the parts together not exposing them for a period of time to the holographic recording process. In this way, environmental conditions that can affect the performance of the holographic recording material may be observed by subsequent attempts to record a hologram. The materials selected for the two parts may be suitably selected to be influenced by particular conditions, e.g. temperature, humidity or exposure to light. In this arrangement, the two parts are kept separate and only joined when monitoring of a condition is required.

The exemplary sensor of the present application uses chain polymerization as an amplification process for detection of a target. One dye molecule and one photon together start a chemical process that begins chain polymerization resulting in the conversion of many thousands of monomer molecules. This signal amplification may be of significant advantage in certain applications where the concentration of analyte Another advantage is that the sensor disclosed herein is not reversible. The exemplary photopolymerizable holographic recording material is particularly suitable for use in the sensor because (a) it is self developing and needs no chemical treatment before the result becomes visible and (b) there is an inherent amplification effect due to the fact that one dye molecule starts a chain polymerization reaction. The sensor provides both quantitative and qualitative information, it may be used easily and quickly with a limited amount of specialist equipment and it can be integrated with different technologies. Moreover, the results may be identified by visual inspection by a user either directly or, depending on the application, additional equipment (e.g. CCD camera and associated image processing equipment and computer software) may be added.

The invention claimed is:

1. A method for forming a selective holographic image, the method comprising the steps of:
   providing at least one of a monomer or a free radical generator together with a binder to form a layer of an inactive non-photosensitive holographic recording material;
   activating only a portion of the layer of inactive non-photosensitive holographic recording material into a photosensitive state by selectively imbibing it with a dye forming a selectively activated photosensitive holographic recording material; and
   recording a holographic image in the activated portion of the layer by exposing at least the selectively activated photosensitive holographic recording material to a holographic recording process where no hologram is formed in other portions of the layer void of any dye and which remains inactive and non-photosensitive.

2. The method of claim 1 wherein the holographic image comprises one or more of the following: a logo, a stamp, a signature or a fingerprint.

3. A selective hologram prepared by a process comprised of the steps:
   providing at least one of a monomer or a free radical generator together with a binder to form a layer of an inactive non-photosensitive holographic recording material;
   activating only a selective portion of the layer of the inactive non-photosensitive holographic recording material into a photosensitive state by imbibing it with a dye forming a selectively activated photosensitive holographic recording material; and
   recording a holographic image in the activated selective portion of the layer by exposing at least the selectively activated photosensitive holographic recording material to a holographic recording process where no hologram is formed in the other portions of the layer which lacks any dye and remains inactive and non-photosensitive.

4. A method of creating a security feature comprising a patterned hologram, the method comprising the steps of:
- providing a dry non-photo sensitive polymer layer comprising a binder, at least one monomer and at least one free radical generator;
- patterning selectively the dry polymer layer with a dye in a pattern of the security feature; and
- exposing the dry polymer layer to a holographic recording process to polymerize the dry polymer layer in a self developing process creating a security feature only where the layer has been patterned with dye and wherein the dry polymer layer outside the patterned portion is non-photo sensitive and lacks any dye.

5. The method according to claim 4, wherein the pattern comprises one or more of the following: a logo, a stamp, a signature or a fingerprint.

6. The method according to claim 4, wherein the dry polymer layer is provided as a sheet.

7. The method according to claim 6, wherein the dye is provided in an ink.

8. The method according to claim 7, where the ink is provided by a printing process.

9. The method according to claim 8, wherein the printing process comprises a printer.

10. The method according to claim 9, wherein the printer is an ink-jet printer.

11. The method according to claim 10, wherein the ink is provided by means of a pen or brush.

12. The method according to claim 4, wherein the security feature is visible to the naked eye.

13. The method according to claim 4, wherein the security feature is observable using infra red light and detection.

14. The method according to claim 4, wherein the holographic recording process comprises exposing the dry polymer layer to an interference pattern provided by at least two beams of coherent light.

15. A security feature comprising a polymer layer in which a patterned hologram is formed, wherein the polymer layer comprises a binder, at least one monomer, and at least one free radical generator, wherein a pattern of the patterned hologram is formed in a first area of the layer in which a dye is present and photo-polymerization has occurred and a second area in which there is no dye present, no photo-polymerization has occurred and no hologram has been formed.

16. The security feature of claim 15 wherein the pattern comprises one or more of the following: a logo, a stamp, a signature or a fingerprint.

17. The security feature according to claim 15, wherein the security feature is visible to the naked eye.

18. The security feature according to claim 15, wherein the security feature is viewable using infra red light.

* * * * *